United States Patent [19]

Foster

[11] Patent Number: 4,506,661
[45] Date of Patent: Mar. 26, 1985

[54] BALANCED SUSPENSION KNEE BRACE

[76] Inventor: Dean J. Foster, 2501 Via Torina, Del Mar, Calif. 92014

[21] Appl. No.: 487,269

[22] Filed: Apr. 21, 1983

[51] Int. Cl.³ .............................................. A61F 5/00
[52] U.S. Cl. ..................................... 128/80 C; 128/88
[58] Field of Search ................... 128/80 C, 80 F, 88, 128/87 R, 165; 2/22, 24

[56] References Cited

U.S. PATENT DOCUMENTS

| | | | |
|---|---|---|---|
| 1,622,211 | 3/1927 | Sheehan | |
| 2,174,719 | 10/1939 | Dresser | 128/80 |
| 2,557,604 | 6/1951 | Invidiato | 128/80 |
| 2,587,166 | 2/1952 | Jovick | 2/24 |
| 3,046,981 | 7/1962 | Biggs et al. | 128/80 |
| 3,387,305 | 6/1968 | Shafer | 2/22 |
| 3,528,412 | 9/1970 | McDavid | 128/80 |
| 3,581,741 | 6/1971 | Rosman | 128/80 |
| 3,669,105 | 6/1972 | Castiglia | 128/80 |
| 4,139,002 | 2/1979 | Almedia | 128/80 |
| 4,240,414 | 12/1980 | Theisler | 128/80 |
| 4,271,831 | 6/1981 | Deibert | 128/80 C |
| 4,361,142 | 11/1982 | Lewis et al. | 128/88 X |
| 4,372,298 | 2/1983 | Lerman | 128/80 C |
| 4,381,768 | 5/1983 | Erichsen et al. | 128/80 C |

Primary Examiner—John D. Yasko
Attorney, Agent, or Firm—Baker, Maxham, Callan & Jester

[57] ABSTRACT

A knee brace for constraining the knee to its natural position and motion includes a femoral band and tibial band connected together by inner and outer rigid bar members pivotally connected together by a floating polycentric hinge joint to permit natural pivoting of the knee and includes a pair of condylar pads for engaging both sides of the knee and a prepatellar pad supported from the condylar pads by derotation straps with further derotation straps securing the prepatellar pad by cross-strap means to opposite ones of the lower bar member. A pair of posterior straps secured to the upper end of the upper bars cross behind the femoral condyles and are connected to opposite ones of the brace hinge members.

13 Claims, 5 Drawing Figures

U.S. Patent   Mar. 26, 1985   4,506,661
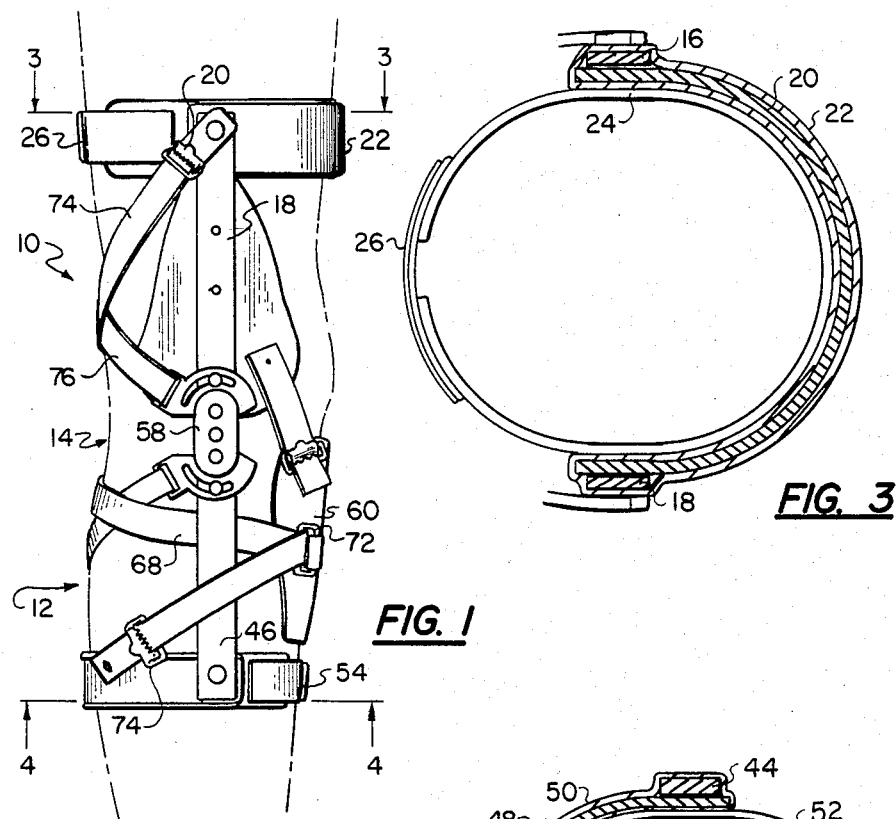
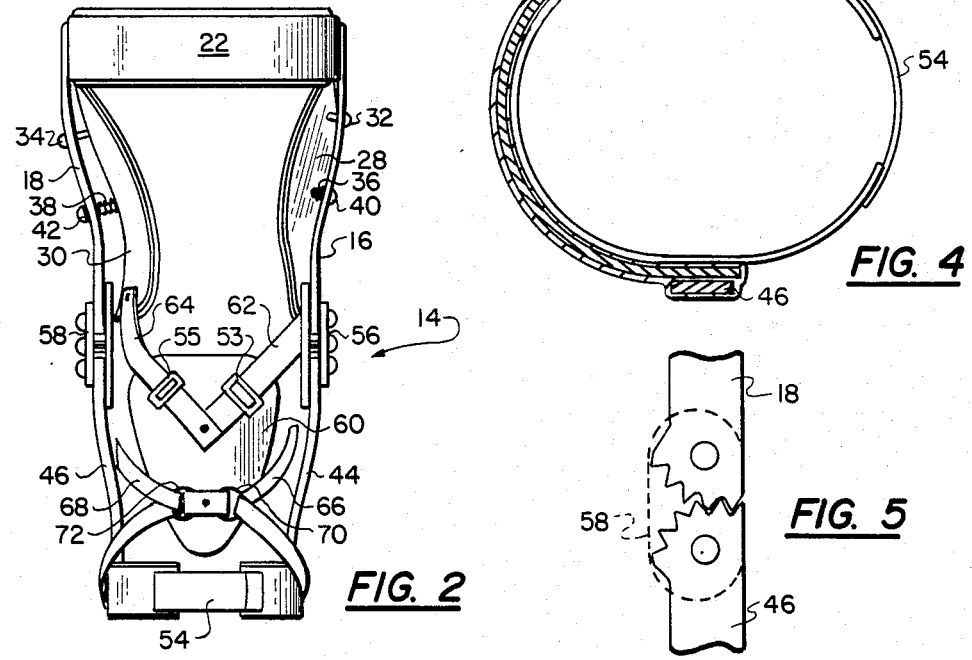

BALANCED SUSPENSION KNEE BRACE

BACKGROUND OF THE INVENTION

The present invention relates to orthopedic brace members and pertains particularly to a multiple stability balanced suspension knee brace.

The human leg has a skeleton structure made up of a lower bone called the tibia, which supports the calf structure and an upper bone called the femur, which supports the thigh structure. These bones are hinged together at a knee joint which consists of femoral condyles supported in engagement with bearing-like pads on the upper end of the tibia known as the lateral meniscus and the medial meniscus. The knee joint is held together by a plurality of ligaments including medial and lateral collateral ligaments and internal ligaments including anterior and posterior cruciate ligaments. The patella is mounted in front of this joint aiding in the leverage necessary for movement or extending of the leg at the knee.

When one or more of the ligaments or other structure of the knee become damaged, the knee joint may become unstable. This may permit the knee to bend or wobble laterally, slip anteriorly or posteriorly, or rotate about its axis. Such instability may result from many forms of injury. In such cases, the knee may be left with a permanent instability. It is therefore desirable to support the knee in a stable position, particularly its natural position, to permit the natural motion thereof.

While many attempts have been made in the past to provide supporting knee braces, many of these, however, while offering certain desirable characteristics, still have certain drawbacks.

The more relevant U.S. Patents directed to knee braces include the following:

U.S. Pat. No. 3,581,741 issued June 1, 1971 to Maurice Roseman entitled "Knee Brace". This patent discloses an upper generally channel-shaped thigh member 18 hingedly connected by hinges 16 and 48 to downwardly depending bar members 84 and 50' which are connected to a lower calf encircling or securing member. A pair of thigh attachment straps encircle the posterior thigh to retain the upper or thigh member into position;

U.S. Pat. No. 3,669,105 issued June 13, 1972 to Castiglia and entitled "Brace For Articulated Limbs". This patent discloses a pair of pads 12 and 14 positioned to engage the outer thigh and calf respectively and connected together by padded bar members hinged together with a cross-over bar hinged at 46 and including a pad 40 for engaging the inside of the knee. A number of flexible straps or bands are provided for securing the structure in position; and U.S. Pat. No. 4,139,002 issued Feb. 13, 1979 to Almedia entitled "Universal Knee Orthosis". This patent discloses an upper or thigh engaging anterior thigh engaging similar tubular member 12 hinged by hinge pins 22 to a lower posterior calf engaging semicircular or semicylindrical member 16 and further includes a lower forward shin cover member 14 pivoted by pivot pins 24 to the lower member 16. Flexible straps are utilized for strapping the upper and lower members to the leg.

While the structures disclosed in the above described patents provide a certain degree of knee stability, they do not provide a balanced suspension constraining the knee against rotation as well as anterior displacement and at the same time permit normal flexing thereof.

It is therefore desirable that an improved multiaxis stabilizing, balanced suspension brace be available which supports and maintains normal knee movement.

BRIEF DESCRIPTION OF THE DRAWINGS

The above and other objects and advantages of the present invention will become apparent from the following description when read in conjunction with the drawings wherein:

FIG. 1 is a side elevation view showing the brace of the present invention in position for use;

FIG. 2 is a front elevation view of the brace of FIG. 1;

FIG. 3 is a section view taken generally on line 3—3 of FIG. 1;

FIG. 4 is a section view taken generally on line 4—4 of FIG. 1; and

FIG. 5 is a detailed view of the joint of the brace of FIG. 1.

DETAILED DESCRIPTION OF A PREFERRED EMBODIMENT

Turning to FIG. 1 of the drawings, the brace of the present invention comprises generally an outer brace and an inner brace. The outer brace comprises an upper brace assembly designated generally by the numeral 10 pivotally or hingedly connected to a lower brace assembly designated generally by the numeral 12 by means of a central hinge assembly designated generally by the numeral 14.

The upper brace assembly includes a substantially rigid medial support bar member 16 and a lateral support bar member 18 connected together by means of a generally U- or C-shaped, substantially rigid strap member 20 connected such as by riveting or the like to the upper ends of the bar members 16 and 18. This structure can be constructed of high strength lightweight metal, such as aluminum and other metals. This part of the structure may also be constructed of high stength plastics, and laminates, such as fiberglass, carbon fibers and the like. The C-shaped strap member constitutes an anterior femoral strap and is preferably padded or covered by a cover 22 which may be a soft leather or similar material and includes an anterior strap of leather or the like 24 for encircling the calf with an attachment strap 26 for securing the ends of the strap 24 together about the thigh.

The inner brace includes a pretibial pad and a pair of condylar pads consisting of a medial condylar pad 28 and a lateral condylar pad 30 secured by riveting at the upper ends such as by rivets 32 and 34 respectively to the bar members 16 and 18. The pads are secured and biased at the lower end thereof by means of a pair of compression springs 36 and 38 respectively into gripping engagement with the bony condylar structure of the femur. The springs 36 and 38 are mounted on pins 40 and 42 supported in the bar member 16 and 18.

The lower brace assembly comprises a medial bar member 44 and a lateral bar member 46 connected together at their lower ends by means of a generally C-shaped posterior tibia strap member 48 which has a generally C-configuration and is connected at opposite ends thereof to the lower ends of the bar members 44 and 46. This frame structure may also be constructed of high strength lightweight metals or high strength lightweight plastic and/or laminates. This generally C- shaped posterior tibia strap is preferably covered by a soft covering 50 such as a soft leather or similar material. A flexible attachment strap 52 is secured on the inside of the strap member 48 for encircling the calf and securing by securing strap 54 into position around the calf.

The upper and lower brace assemblies are hinged together by the polycentric hinge assembly 14 which comprises a medial hinge strap or bar 56 and a lateral bar or strap 58 each including upper and lower pivot pins pivotally connected to the respective upper and lower bars 16 and 44, 18 and 46, which in turn are geared together by sector gears as shown in FIG. 5. The hinge structure and bar members of the brace assembly are not themselves part of this invention, apart from the combination, but are components of the combination which are available from the American Standard Company as a brace assembly.

A prepatellar pad 60 for engaging the tibia below the patellar has a configuration wide at the top tapering down to a narrow rounded tip at the bottom, as generally shown (FIG. 2). The prepatellar pad is supported from the medial and lateral condylar pads 28 and 30 by means of antirotation straps 62 and 64 which include means in the form of buckles 53 and 55 for adjusting the tension and position thereof. These straps 62 and 64 are preferably nonelastic webbing or the like. This prepatellar pad as can be seen in FIG. 1, is positioned just below the patella and in combination with other structure of the brace assembly (antirotation straps 62 and 64, etc.) completes the inner brace and prevents rotation of the femur and tibia relative to one another and applies forces that support them in anterior and posterior alignment.

A pair of posterior calf suspension straps 66 and 68 are connected at their upper ends to the respective lower bracket portion of the respective hinges 56 and 58 and extend through loops 70 and 72 on the lower portion of the prepatellar pad and are adjustably connected by adjustable buckles or the like only one of which, 74, is shown to the tibial strap 48.

Similar anterior thigh suspension straps 74 and 76 are each respectively connected at one end to the upper ends of the hinge members and cross at the back of the thigh above the knee and are connected by adjustable means such as buckles only one, 76, of which is shown at the upper end of the respective medial and lateral bar members 16 and 18.

The hinge joint of this assembly is constructed to have a constantly changing center (polycentric) of rotation closely mimicking the movement of the natural knee to thereby permit the knee to flex in its normal motion. The above described brace structure is constructed and arranged to secure to and secure the calf and thigh of the leg for securely supporting the tibia and femur in lateral and medial angular position and anterior and posterior alignment, while at the same time constraining axial rotation between the tibia and femur. Thus, the above described structure performs the desirable function of providing a stabilizing support of the leg structure by constraining the knee to its natural position and motion through balanced suspension between inner and outer braces.

While I have illustrated and described my invention by means of specific embodiments, it is to be understood that numerous changes and modifications may be made therein without departing from the spirit and scope of the invention as defined in the appended claims.

I claim:
1. A knee brace for constraining the knee to its natural position, and motion, said knee brace comprising:
first hinged bar means including upper and lower rigid bar members pivotally hinged together at one end thereof;
second hinged bar means including upper and lower rigid bar members pivotally hinged together at one end thereof;
a substantially rigid anterior femoral band securing said upper rigid bar members together;
a substantially rigid posterior tibial band securing said lower rigid bar members together;
a prepatellar pad;
antirotation strap means supporting said prepatellar pad from said upper rigid bar members;
flexible restraining strap means securing said prepatellar pad to said lower rigid bar members;
a pair of condylar pads secured to said upper bar members; and means for biasing said pads toward the condylar.

2. The brace of claim 1 wherein said femoral band and said tibial band are generally C-shaped, and further comprising flexible strap means for securing said respective bands in position.

3. The brace of claim 1 including a pair of posterior straps secured to the upper end of said upper bar and crossing anterior of the femur and secured at the other end to said hinge means.

4. The brace of claim 3 including a pair of posterior calf suspension straps connected at the upper ends to said hinge members and crossing back of the tibia and connecting to the post-patellar pad and then at the lower end to said posterior tibial band.

5. The brace of claim 4 wherein said posterior thigh straps and said posterior calf suspension straps are elastic.

6. The brace of claim 5 wherein said first and second bar members and said anterior femoral strap and said posterior tibial strap are constructed of a lightweight, high strength metal.

7. The brace of claim 6 including biasing means comprises an outer stiff, substantially rigid shell and an inner padding layer.

8. A multiaxis stabilizing knee brace for constraining a leg to its natural motion and position, said knee brace comprising:
upper strap means for encircling and securing around the thigh of a leg;
lower strap means for securing around the calf of a leg;
a lateral hinged bar and medial hinged bar secured at opposite ends thereof to said upper strap means and said lower strap means and including a polycentric hinge joint for positioning adjacent to and aligning with the knee joint;
medial and lateral condylar pads secured in opposed relation between said bar members above said hinges and having a lower edge thereof extending proximate the hinge axis of said hinges;
biasing means biasing said condylar pads inward toward one another;
a prepatellar pad disposed forward and slightly below said hinge members;
a pair of antirotation straps supporting said prepatellar pad from said condylar pads;

a pair of upper posterior suspension straps connected to the upper portions of said bar member for crossing behind the femur; and a pair of lower posterior suspension straps secured to the lower portions of said bar members for connecting to said prepatellar pad and said lower bar structure.

9. The brace of claim 8 wherein said condylar pads comprises an outer shell of fiberglass and an inner padding of open cell foam.

10. The brace of claim 8 wherein said prepatellar pad comprises a panel of heavy duty leather having an inner lining.

11. The brace of claim 10 wherein said strap means for supporting said precondylar pad from said patellar pads is adjustable for adjustably positioning the prepatellar pad and for adjusting the pressure thereof.

12. The brace of claim 11 wherein said upper and lower posterior suspension straps are elastic.

13. The brace of claim 12 wherein said upper strap means and said lower strap means each include a substantially rigid semicircular strap member covered with a pliable material and including padding means on the interior thereof.

* * * * *